United States Patent [19]

Borch et al.

[11] Patent Number: 4,908,356
[45] Date of Patent: Mar. 13, 1990

[54] ALDOPHOSPHAMIDE DERIVATIVES USEFUL AS ANTITUMOR AGENTS

[75] Inventors: Richard F. Borch, Pittsford; Ronald R. Valente, Rochester, both of N.Y.

[73] Assignee: Research Corporation Technologies, Inc., Tucson, Ariz.

[21] Appl. No.: 198,429

[22] Filed: May 25, 1988

[51] Int. Cl.⁴ .................. A61K 31/535; C07D 265/06
[52] U.S. Cl. ........................................ 514/90; 544/72; 544/88; 544/96
[58] Field of Search ................ 544/72, 88, 96; 514/90

[56] References Cited

U.S. PATENT DOCUMENTS 4,617,295 10/1986 D'Silva .............................. 544/88 X Primary Examiner—Richard L. Raymond
Attorney, Agent, or Firm—Scully, Scott, Murphy & Presser

[57] ABSTRACT

A compound of the formula

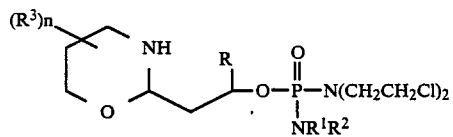

wherein $R^1$ and $R^2$ may be the same of different and are each independently hydrogen or lower alkyl which may be unsubstituted or monosubstituted with halogen, lower alkoxy or hydroxy with the proviso that the substituent is not the α-carbon or $R^1$ and $R^2$ taken together with the carbon to which they are attached form a morpholino ring;

each $R^3$ is independently hydrogen, lower alkyl, carboxy or carbalkoxy;

n is an integer from 0, 1, 2 or 3 and

R is hydrogen, lower alkyl, cycloalkyl, arylalkyl aryl or a nitrogen, sulfur or oxygen containing heterocyclic or a heterocyclic lower alkyl and pharmacuetically acceptable salts thereof.

19 Claims, No Drawings

ALDOPHOSPHAMIDE DERIVATIVES USEFUL AS ANTITUMOR AGENTS

This invention relates to novel aldophosphamide derivatives which have useful pharmaceutical properties and are useful as anti-tumor agents.

BACKGROUND OF THE INVENTION

Cyclophosphamide (also known as cytoxan) is one of the most widely used anti-cancer drugs in the world. It is administered in combination with a number of other drugs to treat a wide variety of hematologic and solid tumors. However, there are several features of the drug that can detract from its clinical efficacy. First, the drug requires metabolic activation in the liver to produce metabolites that are toxic to cancer cells. Second, the drug is specifically toxic to the urinary bladder and also displays the bone marrow toxicity typical of the alkylating agent class of anti-cancer drugs. Third, cyclophosphamide is a potent suppressor of the immune system at the doses used to treat cancer, thus decreasing the infection-fighting ability of patients already debilitated by their disease. Finally, repeated use of cyclophosphamide frequently results in the development of resistance to the drug in a patient's cancer cells, thus rendering the drug ineffective.

The present invention describes new cyclophosphamide compounds that will circumvent one or more of these problems. Compounds included within the present invention are "preactivated", they do not require metabolism in the liver to acquire antitumor activity. The compounds of the present invention are effective in treating tumors in animals that have developed resistance to cyclophosphamide itself. Finally, these compounds are free of the urinary bladder toxicity exhibited by cyclophosphamides.

BRIEF DESCRIPTION OF THE INVENTION

The present invention relates to new chemical open chain aldophosphamides possessing anti-tumor activity. The compounds of the present invention have the formula

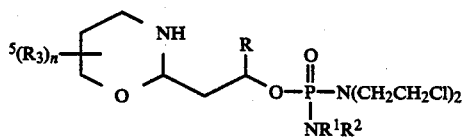

wherein $R^1$ and $R^2$ may be the same or different and are each independently hydrogen or lower alkyl which may be unsubstituted or monosubstituted with halogen or lower alkoxy or hydroxy, with the proviso that the substituent is not on the $\alpha$carbon or $R^1$ and $R^2$ taken together with the nitrogen to which they are attached form a morpholino ring.

R is hydrogen, lower alkyl, aryl, cycloalkyl, arylalkyl or a nitrogen, oxygen or sulfur heterocyclic;

each $R^3$ is independently hydrogen or lower alkyl, carboxy or carbalkoxy and n is 0, 1, 2 or 3 and pharmaceutically acceptable salts thereof.

DETAILED DESCRIPTION OF THE INVENTION

The term $\alpha$carbon refers to the carbon atom that is adjacent to the nitrogen atom of the phosphamide; the term omega carbon refers to the last carbon atom in the alkylene chain, i.e., the carbon which is furthest from the nitrogen.

In the foregoing description, the lower alkyl groups either singly or in combination with other groups contain up to 6 carbon atoms which may be in the normal or branched configuration including methyl, ethyl, propyl, isopropyl, butyl, isobutyl, t-butyl, amyl, pentyl, hexyl and the like. The preferred alkyl groups contain 1 to 3 carbon atoms.

The aryl groups are aromatic rings containing from to 10 ring carbon atoms. The aryl groups include phenyl, $\alpha$-naphthyl and $\beta$-naphthyl. The aryl group is preferably phenyl.

The aralkyl moieties are aromatic groups which are substituted to the phosphamide chain through the alkylene group, said alkylene group containing up to six carbon atoms. Such groups include benzyl, phenethyl, phenylpropyl, 2-naphthylmethyl, and the like. The preferred arylalky group is phenethyl and benzyl.

As employed herein, the expression "nitrogen, sulfur or oxygen heterocyclic ring" is meant to include those heterocyclic rings which include at least one sulfur, nitrogen or oxygen ring atom but which may include one or several of said atoms. The expression also includes saturated and unsaturated heterocylics as well as the heteroarismatic rings. These groups contain from five to ten ring atoms on the heterocyclic moiety. Representative heterocyclics include furan, thiophene, pyrrole, pyridine, pyrazole, pyrazine, pyrimidine, pyridazine, oxazole, quinoline, isoquinoline, indole, benzothiophen, benzofuran, benzoxazole, piperazine, tetrahydrofuran, imidazole and the like. The preferred heterocyclic is pyridyl, especially 3- or 4 pyridyl.

Halo, as defined herein, is bromine, fluorine, iodine and preferably chlorine.

Cycloalkyl as used herein may be mono or bicyclic or polycyclic moieties, containing from 3 to about 20 carbons These groups may be fully saturated or partially unsaturated and may contain from one to three fused rings. These groups include cyclopropyl, cyclobutyl, cyclopentyl, cyclohexyl, cycloheptyl, bornyl, norbornyl adamantyl and the like. Moreover, cycloalkyl as defined herein may also include benzocycloalkyl groups, i.e., a benzene ring fused to a cycloalkyl moiety, e.g., indanyl and the like. The cycloalkyl groups may be mono or di-substituted and carry substituents such as halogen, hydroxy, lower alkyl, lower alkoxy, amino, lower alkylamino, diloweralkylamino, mercapto, thioalkyl, nitro, trifluoromethyl, formyl, lower alkanoyl, carboxy, lower carbalkoxy and the like.

The preferred R groups are hydrogen, methyl, ethyl, phenyl or pyridyl.

The R groups may be unsubstituted or monosubstituted with a variety of substituents, such as lower alkyl, aralkyl, aryl, cycloalkyl, halo, lower alkoxy, nitro, nitrilo, hydroxy, formyl, carboxy, lower alkanoyl, carboxamide, amino, aminoalkyl, alkylamino, dialkylamino, hydroxy, thioalkyl, mercapto, and the like. It is preferred that said substituents be present in the intermediate compounds used in forming the final products. The alkyl groups as well as the heterocyclic groups e.g., pyridyl, is preferably, unsubstituted while the aryl groups, e.g. phenyl, may be unsubstituted or monosubstituted with nitro, halo or alkyl. It is preferred that the substitution of the phenyl be on the para position of the phenyl group. The preferred substituted phenyl groups are p-nitrophenyl, p-tolyl and p-fluorophenyl.

The preferred $R^1$ and $R^2$ groups are hydrogen or substituted alkyl containing up to 3 carbon atoms on the main chain wherein the substituent is an electron-withdrawing group. As used herein, the term electron withdrawing group is a group that will draw electrons to itself more than a hydrogen atom would if it occupied the same position in the molecule. See, March J., "Advanced Organic Chemistry," 2nd. ed., McGraw Hill, N.Y., N.Y., p. 21 (1977). Electron withdrawing groups include lower alkoxy, lower alkanoyl, formyl, lower alkenyl, lower alkynyl, aryl, hydroxy, arylalkyl, hydroxy, mercapto, lower thioalkyl, carboxy, lower carbolkoxy, aryloxy, halo, nitro, cyano, lower trialkylamino and the like. The electron withdrawing groups are preferably located on the omega carbon of $R^1$ or $R^2$, i.e., on the carbon furthest away from the nitrogen. Therefore, the preferred substituents are chloro and ethoxy. The preferred $R^1$ and $R^2$ groups are hydrogen, $CH_2CH_2Cl$, $CH_2CH_2OCH_2CH_3$ or $CH_2CH_2OH$.

As defined herein, $R_1$ and $R_2$ taken together with the nitrogen to which they are attached form a morpholino ring. This is also a preferred value of $R_1$ and $R_2$.

Although $R^1$ and $R^2$ may be different, it is preferred that $R^1$ and $R^2$ be the same.

$R^3$ is preferably lower alkyl, especially methyl. The preferred values of n are 1, 2 or 3. By definition, when n is 0, $(R^3)_n$ is defined to be hydrogen; i.e., the 1,3-oxazin-2-yl ring is unsubstituted. When n is 1, the ring is mono substituted; when n is 2, it is disubstituted, etc.

It is preferred that the 4 position of the 1, 3 oxazin-2-yl ring is substituted, either mono or disubstituted. Especially preferred are 4,4,6 tri-substituted 1,3-oxazin-2-yls. The preferred substituent is methyl. Therefore, the especially preferred compounds of the present invention have the formula

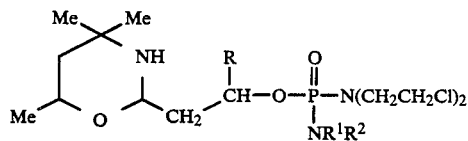

The compounds of the present invention can be prepared by art recognized techniques. The compounds of Formula I can be prepared as outlined in the following scheme:

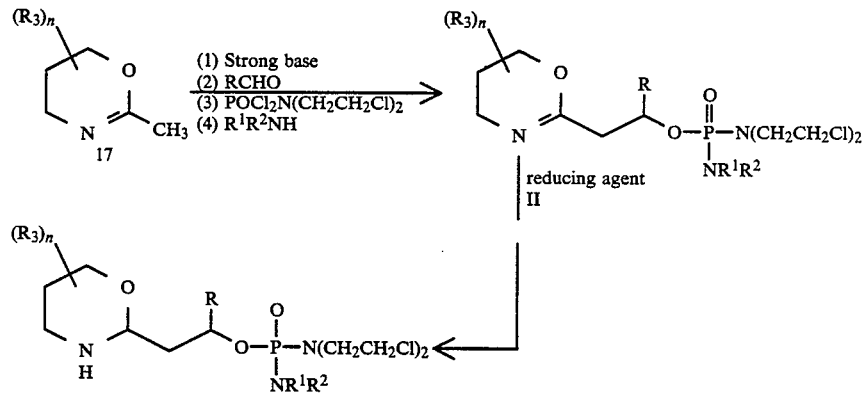

Wherein R, $R^1$, $R^2$, $R^3$ and n are as defined hereinabove.

17 is treated with an organometallic base, such as n-butyllithium, in an inert solvent, such as tetrahydrofuran or ether followed by sequential addition of the aldehyde, in accordance with the procedure in Meyers, et al. Jr. *J. Org. Chem.*, 38, 36 (1983). The product resulting therefrom was reacted with phosphoramide chloride and the amine $R^1R^2NH$ to give the dihydrooxazine II. The dihydrooxazine is reduced with a reducing agent such as sodium borohydride to give a compound of Formula I.

Alternatively, when R is hydrogen the compounds of Formula I can also be prepared by the following reaction pathway:

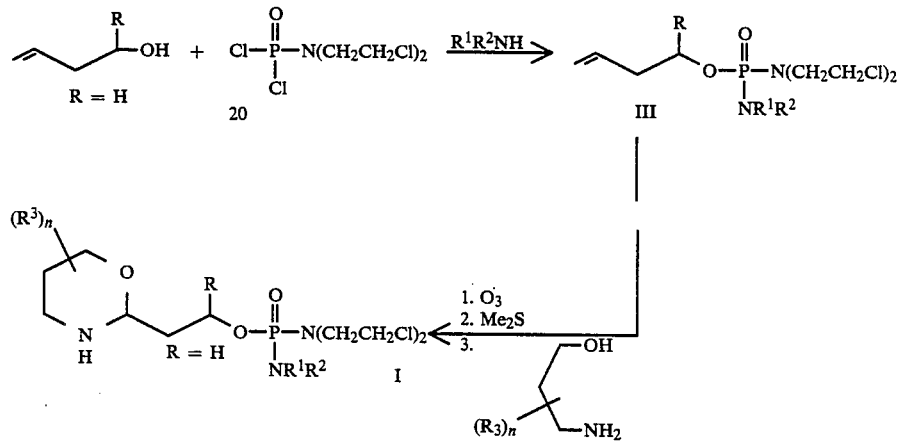

Treatment of 3-buten-1-ol with a strong base such a n-butyllithium, at room temperature and in an inert solvent such as tetrahydrofuran or ether followed by the sequential addition of N,N-bis-(2-chloroethyl)phosphoramide dichloride 20 and an amine $R^1R^2NH$ produces the 0-(3-butenyl)-N,N-bis(2-chloroethyl) phosphorodiamidate derivative of Formula III. The double bond is oxidatively cleaved with ozone and the aldehyde trapped in situ with 2-amino-2-methyl-4-pentanol 18 to provide a compound of Formula I, wherein R is hydrogen.

The present new compounds contain basic nitrogen and can form salts with acids. All such acid salts are contemplated by the invention but especially preferred are salts with pharmaceutically acceptable acids, such as hydrochloric, sulfuric, nitric, toluene, sulfonic, acetic, propionic, tartaric, malic and similar such acids well known in this art. In addition, quaternary salts can be formed using standard techniques of alkylation employing, for example, hydrocarbyl halides or sulfates such as methyl, ethyl, benzyl, propyl or allyl halides or sulfates.

The compounds of the present invention can be administered to the host in a variety of forms adapted to the chosen route of administration, i.e., orally, intravenously, intramuscularly or subcutaneous routes.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Compositions or preparations according to the present invention are prepared so that an oral dosage unit form contains an amount ranging from about 100 mg to about 5 g of active compound. Preferred dosage ranges from about 10 mg to about 500 mg of active compound. Especially preferred dosage ranges from about 25 mg to about 100 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring may be added. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of micro-organisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The following examples further illustrate the invention.

EXAMPLE 1

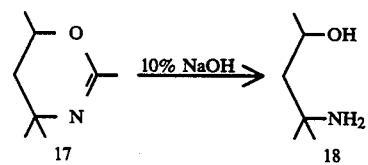

Preparation of 4-Methyl-4-amino-2-pentanol (18).

5,6-Dihydro-2,4,4,6-tetramethyl-4H-1,3-oxazine (21.0 g, 0.15 mol) was refluxed with 80 ml of 10% NaOH in water for 8.5 hrs. The reaction vessel was allowed to cool to room temperature. This mixture was then saturated with sodium chloride, extracted with ether (5×30 ml), and the ether extract dried with solid potassium hydroxide. Removal of solvent under reduced pressure gave an oil which was distilled (b.p 72°–75°, 15 mm) to yield 18 as a clear liquid (16.0 g, 91%). $^1$H NMR (CDCl$_3$) δ4.11 (m, 1H), δ1.38 (m, 2H), δ1.20 (s, 3H), δ1.19 (s, 3H), δ1.14 (d, J - 6.1, 3H) IR (neat) 3350, 3280, , 2970, 2950, 2930, 2900, 2870, 1610, 1465, 1435, 1380, 1365, 1340, 1295, 1260, 1190, 1170, 1130, 1100, 1050, 1000, 970, 925, 905, 880, 835, 760 cm$^{-1}$.

EXAMPLE 2

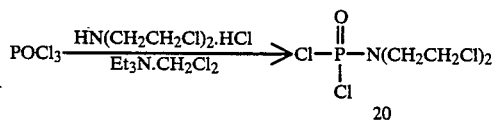

20

Preparation of Bis-(2-chloroethyl)phosphoramide dichloride (20).

A solution of phosphorus oxychloride (15.33 g, 0.10 mol) in CH$_2$Cl$_2$ (80 ml) was cooled to 0°. Bis-(2-chloroethyl)amine hydrochloride (17.85 g, 0.10 mol) was added directly. Triethylamine (30.66 ml, 0.22 mol) was added dropwise with constant stirring at 0° with a steady flow of nitrogen exiting through an aqueous solution of NaHCO$_3$. The reaction was then warmed to room temperature by allowing the ice bath to melt. After stirring for 34 hours, 10% KH$_2$PO$_4$ in water (60 ml) was added. The solution was extracted with CH$_2$Cl$_2$ (3×30 ml) and the combined organic extracts washed again with 10% aq. KH$_2$PO$_4$ (3×20 ml) then dried over MgSO$_4$. Removal of solvent under reduced pressure gave a crude solid which was distilled (b.p. 121°–122°, 0.5 mm) to provide pure 20 (19.3 g, 84%) as a white solid; R$_f$=0.67 (EtOAc:hex 1:2); m.p. 57°–59° C.

$^{31}$P NMR (CHCl$_3$) δ= −7.14 ppm

IR (nujol) 1290, 1275, 1260 1220 (P=), 1195, 1160, 1150, 1110, 1095, 1060, 1030, 1010, 980, 975, 940, 920, 885, 850, 770, 750, 710, 665 cm$^{-1}$.

EXAMPLE 3

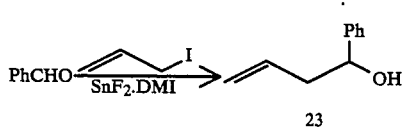

23

Preparation of 1-phenyl-3-buten-1-ol (23).

A suspension of stannous fluoride (3.45 g, 0.022 mol) allyl iodide (3.36 g, 0.02 mol) and benzaldehyde (1.70 g, 0.016 mol) in 60 ml of 1,3-Dimethyl-2-imidazolidinone (DMI) was stirred for 1 hour at room temperature. Water was added to the reaction and the solution was extracted with ether (3×50 ml). The combined organic extracts were washed with brine (1×50 ml), dried over MgSO$_4$ and concentrated. The resulting oil was subjected to flash chromatography with 1.5 EtOAc:hexanes as mobile phase to give pure 23 (2.69 g, 91%) R$_f$ 0.71 (EtOAc:hex 1:2)

$^1$H NMR (CDCl$_3$) δ7.35 (m,5HO), δ5.80 (m, 1H), δ5.16 (m, 2H) δ4.73 (m, 1H), δ2.51 (m, 2H) δ2.06 (br s, 1H). IR (neat) 3400, 3070, 3025, 3000, 2975, 2930, 2905, 2870, 1725, 1640, 1600, 1490, 1450, 1430, 1370, 1305, 1245, 1195, 1110, 1070, 1040, 1025, 1000, 940, 915, 870, 845, 825, 760, 700, 640 cm$^{-1}$.

EXAMPLE 4

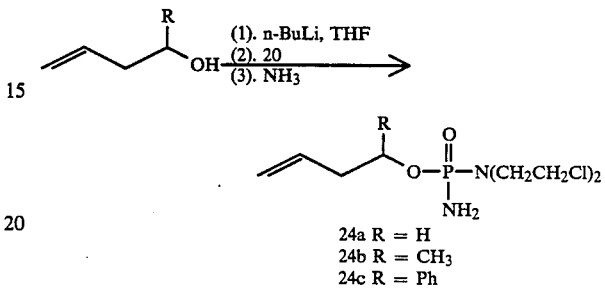

24a R = H
24b R = CH$_3$
24c R = Ph

General preparation of compounds 24a–24c

A solution of the butenyl alcohol (2.0 mmol) in THF (10 ml) was treated dropwise with n-BuLi (1.48 ml. 1.1 eq) at room temperature. After 30 min, the solution was transferred via cannula to a 25 ml addition funnel. The alkoxide was then added dropwise at 0° to a flask which had first been charged with the cyclophosphamide (485 mg, 2.1 mmol) and THF (5.0 ml). The reaction was stirred at 0° for 30 min after the addition was complete. Gaseous ammonia was bubbled through the mixture at 0° for 10 minutes and the resulting milky solution warmed to room temperature as the ice bath was allowed to melt. After stirring at room temperature for 2 hrs, the ammonium chloride was removed by filtration through celite and the solvents removed under reduced pressure.

0-(3-Butenyl)-N,N-bis(2-chloroethyl)phosphorodiamidate (24a).

A yellow oil (510 mg, 93%) was obtained. This compound could be used directly without further purification. An analytical sample was obtained using flash chromatography with 1:1 CH$_2$Cl$_2$:acetone as mobile phase to produce a white solid which melts at room temperature; R$_f$ 0.42 (CH$_2$Cl$_2$:acetone 1:2).

Anal. Calcd for C$_8$H$_{17}$Cl$_2$N$_2$O$_2$P: C, 34.93; H, 6.23; N, 10.18.

Found: C, 35.15; H, 6.39; N, 9.91.

$^1$H NMR (CDCl$_3$) δ5.79 (m, 1H), δ5.15 (m, 2H), δ4.04 (m, 2H), δ3.64 (5, J =6.6, 4H), δ3.43 (m, 4H), δ2.78 (br s, 2H), δ2.42 (m, 2H).

$^{31}$P NMR (CHCl$_3$) δ9.30.

IR (neat) 3440, 3240, 3100, 3000, 2960, 2890, 1640, 1560, 1445, 1530, 1375, 1340, 1300, 1220, 1145, 1130, 1085, 980, 920, 885, 820, 770, 745, 695, 650 cm$^{-1}$.

0-(1-Methyl-3-butenyl)-N,N-bis(2-chloroethyl)phosphorodiamidate (24b).

A pale yellow oil (549 mg. 95%) was obtained and was subjected to flash chromatogrphy with 2:1 CH$_2$Cl$_2$:acetone as mobile phase. The resulting oil was triturated with pet. ether to give a white solid (520 mg; m.p. 53°–55°); R$_f$ 0.40 (CH$_2$Cl$_2$ acetone 2:1).

Anal. Calcd. for $C_9H_{19}Cl_2N_2O_2P$: C, 37.39; H, 6.62; N, 9.69.

Found: C, 37.32; H, 6.69; N, 9.54.

$^1H$ NMR (CDCl$_3$) δ5.79 (m, 1H), δ5.15 (m, 2H), δ4.57 (m, 1H), δ3.64 (t, J =6.5, 4H), δ3.42 (m, 4H), δ2.65 (br s, 2H), δ2.36 (m, 2H), δ1.34 (d, J =6.3, 3H).

$^{31}P$ NMR (CHCl$_3$) δ−10.19, −10.29.

IR (nujol) 3310, 3230, 3120, 1640 1565, 1540, 1300, 1245, 1200, 1170., 1120, 1080, 1060, 1035, 1000, 980, 940, 920, 780, 765, 740, 720 cm$^{-1}$.

O-(1-Phenyl-3-butenyl)-N,N-bis(2-chloroethyl)phosphorodiamidate (24c).

A pale yellow oil (646 mg. 92%) was isolated. This compound could be used directly without further purification. Flash chromatography was used to prepare an analytical sample with 3.2 CH$_2$Cl$_2$:acetone as mobile phase which gave 24c as a white solid (m.p. 65°–67°); R$_f$ 0.50 (CH$_2$Cl$_2$:acetone 2:1).

Anal. Calcd. for $C_{14}H_{21}Cl_2N_2O_2P$: C, 47.88; H, 6.03.
Found: C, 47.75; H, 6.16.

$^1H$ NMR (CDCl$_3$) δ7.36 (m, 5H), δ5.71 (m, 1H), δ5.36 (d of t, $J_t$=6.0, $J_p$=8.2, 1H), δ5.11 (m, 2H), δ3.37 (m, 4H), δ3.12 (m, 4H), δ2.68 (br s, 2H), δ2.65 (m, 2H).

$^{31}P$ NMR (CHCl$_3$) δ−9.77; (acetone) δ−8.05, δ−8.15.

IR (njuol) 3360, 3250, 3140, 1660, 1550, 1305, 1290, 1250, 1210, 1150, 1130, 1080, 1015, 990, 960, 930, 920, 860, 840, 780, 755, 740, 720, 690, 630 cm$^{-1}$.

EXAMPLE 5

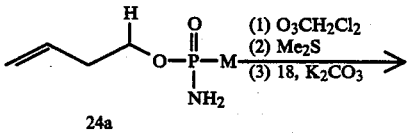

24a

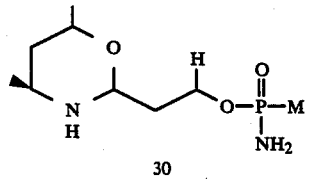

30

M = N(CH$_2$CH$_2$Cl)$_2$

Preparation of
O,[2-(4,4,6-Trimethyltetrahydro-1,3-oxazin-2-yl)-ethyl]-N,N,-bis(2-chloroethyl)phosphorodiamidate (30).

The butenyl compound 24a prepared in Example 4 (10.0 g, 36.0 mmol) was dissolved in CH$_2$Cl$_2$ (150 ml) and cooled to −50°. Ozone was bubbled through the solution for approximately 20 min until a blue color was evident. After additional 2 min, nitrogen was bubbled through the solution for 5 min. The ozonide was treated with methyl sulfide (15.66 g, 252 mmol) at −30°, followed by immediate addition of aminoalcohol 18 as prepared in Example 1 (8.44 g, 72.0 mmol) in CH$_2$Cl$_2$ (20 ml) and solid anhydrous potassium carbonate (13.82 g, 100 mmol). The reaction was warmed to room temperature as the ice bath was allowed to melt, and stirring was maintained for 3 hrs. The potassium carbonate was removed by filtration, the filtrate concentrated, and the resulting oil chromatographed with 9:1 acetone:5-BuOH as mobile phase, to yield 30 (2.97 g, 22%) as a 1:1 mixture of diastereomers; R$_f$0.20, 0.26 (acetone:t-BuOH 9:1). Anal. Calcd. for $C_{13}H_{28}Cl_2N_3O_3P$: C, 41.50; H, 7.50.

Found: C, 41.85; H, 7.47.

$^1H$ NMR (CDCl$_3$) δ4.40 (m, 1H), δ4.19 (m, 1H), δ4.07 (m, 1H), δ3.78 (m, 1H), δ3.64 (t, J=6.8, 4H), δ3.43 (m, 4H), δ3.04 (br s, 2H), δ1.89 (m, 2H), δ1.43 (m, 1H) δ1.18 (m, 10H).

$^{31}P$ NMR (CHCl$_3$) δ−8.42, −8.53.

IR (neat) 3440, 3275, 3120, 2970, 2950, 2930, 2900, 2870, 1715, 1570, 1470, 1445, 1375, 1365, 1320, 1295, 1210, 1180, 1165, 1130, 1085, 1070, 1045, 980, 930, 880, 860, 825, 790, 765, 750, 640 cm$^{-1}$.

EXAMPLE 6

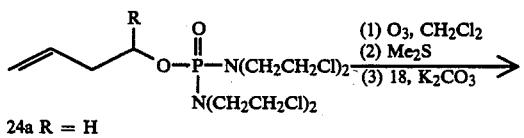

24a R = H
24b R = Ph

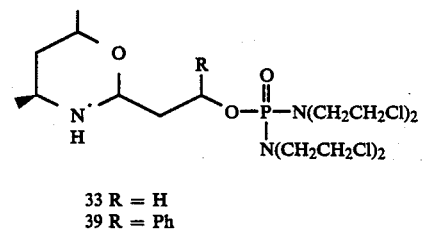

33 R = H
39 R = Ph

Preparation of
O-[2-(4,4,6-Trimethyltetrahydro-1,3-oxazin-2-yl)ethyl]-N,N,NN'-tetrakis(2-chloroethyl)phosphorodiamidate (33).

A solution of crude butenyl derivative 24a prepared in Example 4 (500 mg., 1.25 mmol) in CH$_2$Cl$_2$ (15 mol) was ozonized in the manner described in the preparation of 30. After filtration of the potassium carbonate, the filtrate was treated with dilute aqueous base (1×25 ml) and extracted with ether (3×25 ml). The combined ether extracts were washed with brine (1×25 ml), dried over potassium carbonate and filtered. The solvents were removed under reduced pressure and the resulting thick oil was purified via flash chromatography with 1:1 CH$_2$Cl$_2$:acetone as mobile phase to afford 33 (..210 mg, 33% from starting alcohol); R$_f$ 0.40 (CH$_2$Cl$_2$:acetone 2:1). $^1H$ NMR (CDCl$_3$) δ4.38 (m, 1H), δ4.15 (m, 2H), δ3.78 (m, 1H), δ3.64 (m, 8H), δ3.42 (m, 8H), δ1.89 (m, 2H), δ1.45 (m, 1H), δ1.14 (m, 10H).

$^{31}P$ NMR (CHCl$_3$) δ−9.06.

IR (neat) 3420, 3280, 2970, 2920, 2890, 2870, 1440, 1360, 1340, 1310, 1250, 1220, 1180, 1150, 1130, 1080, 1040, 995, 960, 920, 890, 860, 845, 760, 720, 655 cm$^{-1}$.

Preparation of
O-[1-Phenyl-2-(4,4,6-trimethyltetrahydro-1,3-oxazin-2-yl)ethyl]-N,N-N',N'-tetrakis(2-chloroethyl)phosphorodiamididate (39).

A solution of butenyl derivative 24b (1.0 g. 2.10 mmol) in CH$_2$Cl$_2$ (30 ml) was ozonized following the same procedure used for the preparation of compound 3. Purification of the resulting oil using flash chromatogrphy with 1:1 EtOAc:hexanes as mobile phase gave 39 (540 mg, 45%) as a 1:1 mixture of diastereomers; $R_f$ 0.38, 0.54 (EtOAc:hex 2:1).

$^1$H NMR (CDCl$_3$) δ7 30 (m, 5H), δ5.52 (m, 1H), δ4.03 (m, 0.5H), δ3.80 (m, 0.5HO, δ3.57 (m, 4H), δ3.31 (m, 8H), δ2.99 (m, 4H), δ2.22 (m, 1H), δ2.01 (m, 1H), δ1.25 (m, 1H), δ1.10 (m, 10H).

$^{31}$P NMR (CDCl$_3$) δ−9 37,δ−9.45.

IR (neat) 3400, 3280, 3100, 3070, 3050, 3020, 2970, 2920, 2890, 2870, 1675, 1625, 1445, 1360, 1340, 1310, 1215, 1180, 1145, 1120, 1080, 1040, 970, 920, 750, 700, 660 cm$^{-1}$.

EXAMPLE 7

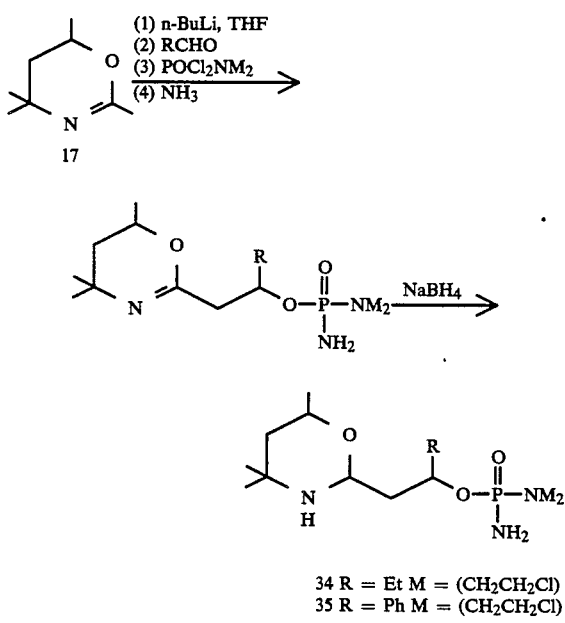

34 R = Et M = (CH$_2$CH$_2$Cl)
35 R = Ph M = (CH$_2$CH$_2$Cl)

Preparation of the anion of 5,6-Dihydro-2,4,4-6-tetrahydro-4H-1,3-oxazine (17).

In a 25 ml three-necked flask which had been successively evacuated and flushed with nitrogen, a solution of 17 (500 mg, 3.54 mmol) in THF (3.6 ml) was cooled to −78° and treated with n-BuLi (2.43 ml. 1.1. eq) over a period of one hr. Approximately 1 hr after the addition was complete a yellow precipitate formed which indicated complete anion formation.

General procedure for the alkylation of the anion.

A solution of the aldehyde (3.89 mmol) in THF (5 ml) was added dropwise to the lithiooxazine at −78° over a period of 30 min. The reaction mixture was allowed to warm slowly to 0°. The resulting alkoxide was then treated with the phosphoryl dichloride (3.89 mmol) all at once either as a solid or as a solution in THF (5 ml). After stirring at 0° for 15 min. gaseous ammonia was bubbled through the reaction mixture for 15 min and the milky solution warmed to room temperature as the ice bath was allowed to melt. The ammonium chloride salts were removed by filtration through celite, the filtrate concentrated and the resulting oil reduced immediately.

General method for reduction of dihydro-1,3-oxazines.

The oil obtained above was dissolved in 95% ethanol (10 ml) and THF (10 ml) and the solution was cooled to between −35° and −40°. A solution of sodium borohydride (144 mg, 3.89 mmol) was prepared by dissolution in a minimal amount of water (2 ml) to which one drop of 40% sodium hydroxide was added. The sodium borohydride solution was added via pipette, the pH maintained between 6–8 by periodic checks with pH paper and addition of 9N hydrochloric acid, and the temperature was maintained between −35° and −45° during addition. After addition was complete, the reaction mixture was stirred for an additional 1 hr (as the temperature and pH were carefully monitored). The solution was then poured onto ice (10 g) and made basic by the addition of 40% aqueous sodium hydroxide (pH 10). The layers were separated, and the aqueous portion was extracted with ether (3×20 ml). The combined organic extracts were washed with brine (1×50 ml) and dried over potassium carbonate. Filtration and concentration gave the crude tetrahydrooxazine.

0-[1-Ethyl-2-(4,4,6-trimethyltetrahydro-1,3-oxazin-2-yl)ethyl]-N,N-bis(2-chloroethyl)phosphorodiamidate (34).

The yellow oil obtained was purified using flash chromatography with 2:3 CH$_2$Cl$_2$:acetone as mobile phase to yield 34 (478 mg, 34%) as a mixture of diastereomers; $R_f$ 0.30, 0.37 (CH$_2$Cl$_2$:acetone 1:2).

$^1$H NMR (CDCl$_3$) 4.42, 3.78 (m, 1H),δ3.62 (t, J=6.8, 4H), δ3 40 (m, 4H), δ1.78 (m, 4H), δ1.45 (m, 1H), δ1.15 (m, 10H), δ0 93 (t, J=6.0. 3H).

δ$^{31}$P NMR (CHCl$_3$) δ−8.51,δ−8.74.

IR (nujol) 3280, 3210, 3100, 1580, 1320, 1295, 1255, 1220, 1175, 1160, 1140, 1080, 1005, 890, 845, 780, 745, 690, 650, 630 cm$^{-1}$.

0-[1,Phenyl-2-(4,4,6-trimethyltetrahydro-1,3-oxazin-2-yl)ethyl], N,N,-bis(2-chloroethyl)phosphorodiamidate (35).

The crude oil consisted of two major diastereomers (92% of products as determined by $^{31}$P NMR) and was purified via flash chromatography using 2:3 CH$_2$Cl$_2$:acetone as mobile phase to produce 35 (831 mg, 52%) as an oil. The two major isomers could be separated using 1:1 CH$_2$Cl$_2$: acetone as mobile phase; $R_f$0.45, 0.36 (CH$_2$Cl$_2$:acetone 1:2).

Anal. Calcd. for C$_{19}$H$_{32}$Cl$_2$N$_3$O$_3$P: C, 50.54; H, 7.13; N, 9.29.

Found: C, 51.09; H, 7.41; N, 9.14.

$^1$H NMR (CDCl$_3$) δ7.35 (m, 5H), δ5.48 (m, 1H), δ4.35 (t, J=6.0, 0.5H) δ4.25 (t, J=6.1, 0.5H) δ3.43 (m, 4H), δ3.20 (m, 4H), δ2.31 (m, 1H), δ1.91 (m, 1H), δ1.42 (m, 1H) δ1.14 (m, 10H).

$^{31}$P NMR (CHCl$_3$) δ−8.94,δ−9.02.

IR (neat) 3400, 3260, 3100, 3080, 3050, 3030, 2970, 2920, 2890, 2870, 1675, 1620, 1560, 1445, 1365, 1345, 1320, 1225 (P=O), 1180, 1145, 1120, 1080, 1035, 975, 920, 850, 835, 775, 740, 700, 650 cm$^{-1}$.

EXAMPLE 8

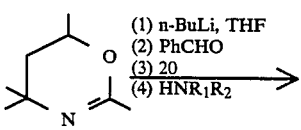

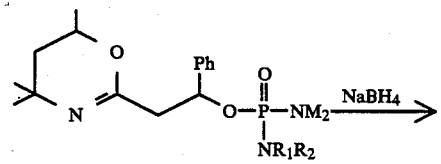

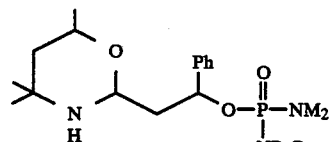

37 R = Me  M = (CH₂CH₂Cl)
38 NR₁R₂

Preparation of O-[1-Phenyl-2-(4,4,6-trimethyl-1,3-oxazin-2-yl)-ethyl]-N,N-bis(2-chloroethyl)-N',N'-dimethylphosphoro diamidate (37).

The same general procedure for the alkylation of the lithiooxazine as described above was used with slight modification. Excess dimethylamine (5 eq) was added all at once to the cooled (0°) solution in place of gaseous ammonia and the reaction warmed to room temperature as the ice bath was allowed to melt. The reaction mixture was treated with a 10% solution of KH₂PO₄ in water (1×30 ml) and the layers were separated. The aqueous portion was extracted with ethyl acetate (3×20 ml) and the combined organic extracts washed with brine (2×25 ml), dried over MgSO₄ and filtered. The solvents were removed under reduced pressure and the resulting dihydrooxazine reduced as described above. The crude tetrahydrooxazine obtained was purified via flash chromatography with 2:1 CH₂Cl₂:acetone as mobil phase. The purified product, 37 (587 mg. 35%) was a 1:1 mixture of diastereomers;

$R_f$ 0.28, 0.35 (CH₂Cl₂:acetone 2:1).

¹H NMR (CDCl₃) δ7.36 (m, 5H) δ5.54 (m, 1H), δ4.18 (t, J=6.9, 0.5H) δ3.03 (m, 0.5H), δ3.64 (m, 1H) δ3.33 (m, 4H), δ3.03 (m, 4H), δ2.70 (d, J=10, 6H) δ2.26 (m, 1H), δ2.03 (m, 1H) δ1.41 (m, 1H), δ1.12 (m, 10H).

³¹P NMR (CHCl₃) δ−7.65, δ−7.81.

IR (neat) 3300, 3100, 3080, 3050, 3030, 2970, 2920, 2890, 2870, 2800, 2220, 1675, 1625, 1470, 1450, 1370, 1300, 1215, 1165, 1145, 1120, 1080, 1040, 970, 915, 835, 750, 730, 700, 669, 640 cm⁻¹.

EXAMPLE 9

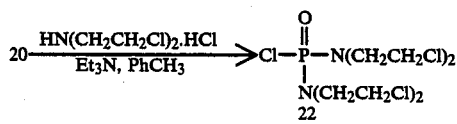

Preparation of N,N,N',N'-Tetrakis-(2-chloroethyl)phosphorodiamidic chloride (22).

To a stirred suspension of bis-(2-chloroethyl)phosphoramidic dichloride, 20 (5.18 g, 20.0 mmol) prepared in Example 2 and bis-(2-chloroethyl)amine hydrochloride (3.93 g, 22.0 mmol) in dry toluene (200 ml) was added triethylamine (6.13 ml. 44 mmol) at room temperature. After addition was complete, the mixture was heated to reflux. Reflux was maintained for 16 hours. The cooled (r.t) solution was extracted with 10% aq. KH₂PO₄ (2×100 ml) and the aqueous portions extracted with ether (2×50 ml). The combined organic extracts were washed with brine (1×100 ml) and dried over MgSO₄. Filtration and concentration gave a brown serum which was subjected to flash chromatography with 3:1 hexanes:EtOAc as mobile phase. The resulting solid (4.01g, was recrystallized from ether/petether. m.p.=48°-49°

$R_f$ 0.40 (EtOAc:hex 1:2)

Anal. Calcd. for C₈H₁₆Cl₅N₂OP: C, 26.36; H, 4.43. Found: C, 26.75; H, 4.40

¹NMR δ3.72 (m, 8H), δ3.56 (m, 8H).

³¹P NMR=δ+0.66

IR (nujol) 1260, 1235, 1220 (P=O), 1195, 1140, 1110, 1075, 1015, 1000, 970, 915, 895, 775, 760, 745, 680, 650 cm⁻¹.

EXAMPLE 10

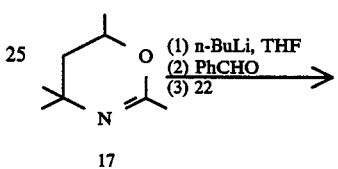

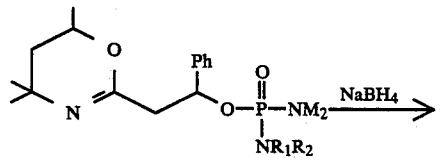

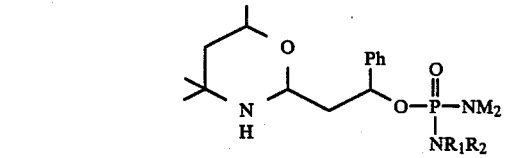

R₁ = R₂ = M = CH₂CH₂Cl

Preparation of O-[1-Phenyl-2-(4,4,6-trimethyltetrahydro-1,3-oxazin-2-yl-ether]-N,N,N',N'-tetrakis(2-chloroethyl)phosphorodiamidate (39).

Using the procedure described in Example 7, the anion of 17 (500 mg, 3.54 mmol) was reacted with benzaldehyde (413 mg, 3.89 mmol). The phosphoramide monochloride 22 prepared in Example 9 (1.42 g, 3.89 mmol) was added all at once to the resulting alkoxide at 0°. Stirring was maintained as the mixture slowly warmed to room temperature. The solution was then heated to reflux for 2 hrs. The cooled (r.t.) solution was then transferred to a 100 ml r.b. flask containing 95% ethanol (30 ml) and cooled to −40°. This solution was reduced with sodium borohydride in the normal manner. The resulting crude reaction product was chromatographed using 1:1 EtOAc: hexanes as mobile phase to give pure 39 (910 mg. 45%) as a mixture of diastereomers; $R_f$ 0.38, 0.54 (EtOAc:hex 2:1).

¹H NMR (CDCl₃) δ7.30 (m, 5H), δ5.52 (m, 1H) δ4.03 (m, 0.5H), δ3.80 (m, 0.5H) 3.57 (m, 4H) δ3.31 (m, 8H),

δ2.99 (m, 4H), δ2.22 (m, 1H) δ2.01 (m, 1H) δ1.25 (m, 1H), δ1.20 (m, 10H).

$^{31}$P NMR (CHCl$_3$) δ−9.37,δ−9.45.

IR (neat) 3400, 3280, 3100, 3070, 3050, 3020, 2970, 2920, 2890, 2870, 1675, 1625, 1445, 1360, 1340, 1310, 1215, 1180, 1145, 1120, 1080, 1040, 970, 920, 750, 600, 660 cm$^{-1}$.

The compounds of the present invention are effective anti-tumor agents. Moreover, the compounds of the present invention do not possess the disadvantage concomitant with the use of cyclophosphamide.

Cyclophosphamides (1) is a probing; it requires metabolism in the liver to acquire anti-tumor activity. More specifically, through the intervention of a hepatic mixed function oxidase, the cyclophosphamide must be activated to form 4-hydroxy cyclophosphamide of unknown stereochemistry ($\frac{2}{3}$), which in turn forms an open chain aldophosphamide, (4) as shown below. It is believed that the aldophosphamide undergoes β-elimination in vivo to produce the active form, phosphoramide mustard 6 (PDA). However a side product of this process is acrolein 7. It is known that acrolein is the metabolite responsible for cyclophosphoramides bladder toxicity known as hemorrhagic cystitis.

These reactions are summarized below.

developed a resistance to cyclophosphamide. This probably occurs by enzyme inactivation of the aldophosphamide intermediate metabolite. This effect is not exhibited by compounds of the present invention.

Therefore, the compounds of the present invention will deliver the same anticancer metabolite as cyclophosphamides, namely phosphoramide mustard, but will not produce the bladder toxin acrolein and more importantly, will not serve as a substrate for the drug inactivating enzyme in the tumor cell.

The compounds of the present invention are effective anti-tumor agents. Cytotoxic evaluation of the compounds of the present invention are determined as follows:

In Vitro Cytotoxic Activity:

A soft agar colony-forming assay according to the procedure of Chu and Fischer, *Biochem. Pharmacol.*, 17, 753–767 (1968) was prepared. Cultured cyclophosphamide resistant L1210 and P388 cells were obtained from Dr. Robert Struck of Southern Research Institute, Birmingham, Ala. Typically, the desired cells (2–3×10$^6$ cells/ml) in exponential growth and suspended in 6.5 ml of Fischer's medium (Gibco Lab., Grand Island, N.Y.) were divided into six groups (1 control and 5 treated groups) containing an equal number of cells in 1 ml.

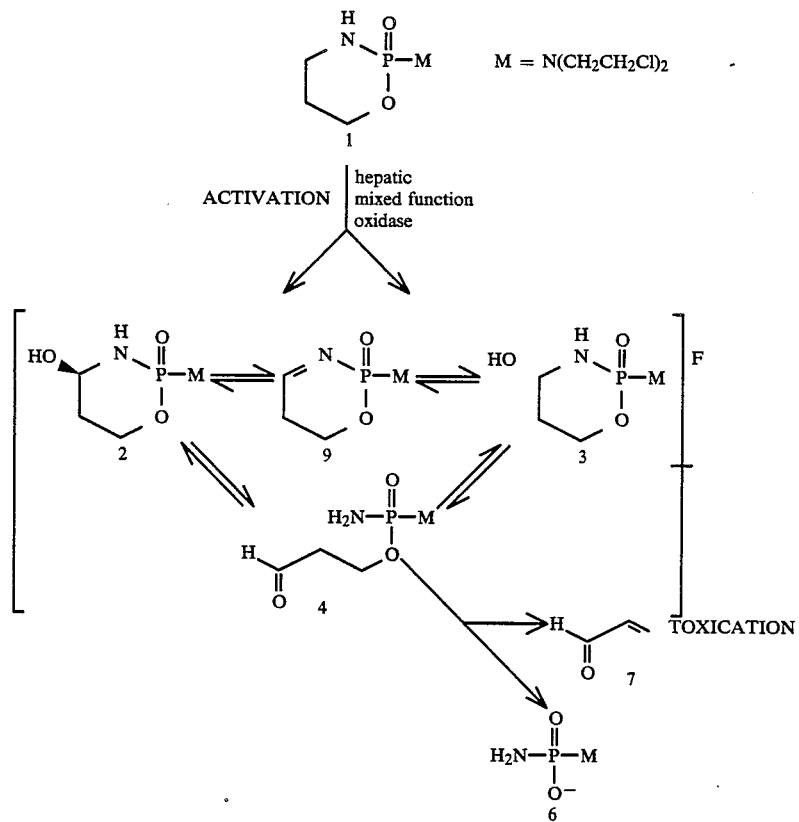

Unlike cyclophosphamide, the compounds of the present invention are preactivated, i.e. they do not require oxidation in the liver to acquire anti-tumor activity to produce the phosphamide mustard. Moreover, no acrolein is produced as a side product from the compounds of the present invention and therefore the risk of cyclophosphamide bladder toxicity is eliminated.

The compounds of the present invention are even more efficacious relative to cyclophosphamide for yet another reason. It has been found that tumor cells have These cells were then treated with varying doses of drug (solution of perhydrooxazine in media or 20% ethanol-water), diluted with media to give a total volume of 10 ml, and incubated for one hour at 37° C. The cells were washed three times with 3 ml of supplemented Fischer's medium (containing 10% horse serum) by centrifuge (800 x g), removal of media by suction, and resuspension of the pellet in media (5 ml). A 1-ml portion was used to determine the cell count with a Coulter counter. From the remainder, a 5-ml suspension of cells was prepared at a density of $10^5$ cells/ml, and between $10^2$ and $10^5$ cells were plated on soft agar and incubated at 37° C. Colonies were counted after 10 days. The log of the surviving fraction was plotted vs. drug concentration and from this plot the $LC_{99}$ was obtained.

The cytotoxic activity of representative compounds of the present invention against both sensitive and cyclophosphamide-resistant (L 1210 and p 388) tumor lines are summarized hereinbelow in Table 1. The $LC_{99}$ value represents the concentration of drugs necessary to effect a 99% cell kill.

In Vitro Cytotoxic Evaluation of New Compounds Against Cyclophosphamide-sensitive (/O) and -resistant (/CP) L1210 and P388 Murine Leukemia Cells.

cyclophosphamide-resistant cells, in contrast to the reference activated cyclophosphamide. This is apparent from the number of new analogs that have resistance factors in the 1–2 range, again in marked contrast to the 10- or 17-fold higher dose of activated cyclophosphamide required to kill the resistant cells. Compounds of the present invention exhibit high potency and activity against cyclophosphamide-resistant cels.

In Vivo Antitumor Activity:

Typically 4 groups of 10 male $B_6D_2F_1$ mice (Jackson Breeding Lab., Bar Harbor Me.) were injected i.p. with $1 \times 10^5$ L1210 tumor cells. Twenty four hours after injection three groups were treated (i.p injection) with varying doses of drug, and the fourth group received the vehicle alone. The mice were observed daily and death dates were recorded. The experiment was termi-

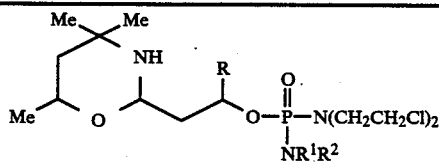

| | | | \multicolumn{6}{c}{$LC_{99}$ Value (μM)} | | | | | |
|---|---|---|---|---|---|---|---|---|
| | | | | L1210 | | | P388 | |
| | | | /O | /CP | RF[a] | /O | /CP | RF[a] |
| | Cyclophosphamide (ref.) | | 8 | 141 | 17 | 6 | 60 | 10 |
| R | $R^1$ | $R^2$ | | | | | | |
| H | H | H | 21 | 145 | 6.9 | 15 | 92 | 6.1 |
| H | $CH_2CH_2Cl$ | $CH_2CH_2Cl$ | 7 | 19 | 2.7 | 5 | 9 | 1.8 |
| H | $R^1 R^2$ taken together with the nitrogen to which they are attached form a morpholino ring. | | 82 | 150 | 1.9 | 53 | 117 | 2.2 |
| $CH_3$ | H | H | 82 | 152 | 1.9 | 64 | 99 | 1.5 |
| $CH_2CH_3$ | H | H | 98 | 170 | 1.7 | 61 | 81 | 1.3 |
| Phenyl | H | H | 14 | 17 | 1.2 | 8 | 9 | 1.1 |
| Phenyl | $CH_2CH_2Cl$ | $CH_2CH_2Cl$ | 4 | 5 | 1.3 | 3 | 3 | 1.0 |
| Phenyl | $R_1$ and $R_2$ together with the nitrogen to which attached form a morpholino group | | 28 | 38 | 1.4 | 12 | 22 | 1.8 |

[a]resistance factor RFS ratio of $LC_{99}$ in resistant/sensitive cells.

The data in Table 1 show substantial variation in antitumor activity depending upon the nature of both the R substituent and the groups attached to the phosphoramide nitrogen. Because the data reports the minimum concentration of drug needed to destroy 99% of the clonogenic cells after a 1-hour exposure, greater potency is represented by a smaller $LC_{99}$ value. The second point to note is that many of the compounds are almost as toxic to both cyclophosphamide-sensitive and nated on day 30 and median survival time (days) and % T/C (ratio of median survival time of treated group divided by the mean survival time of the control group) was calculated. The drug was delivered using either an isotonic saline solution or a carboxymethyl cellulose suspension depending on the solubility of the drug.

The result of the In Vivo studies are tabulated hereinbelow:

TABLE 2

Antitumor Activity of Oxazine Derivatives of Cyclophosphazide Against L1210 Leukemia in BDF, Mice.

| Cmpd. R | M = ($CH_2CH_2Cl$) $R^1$ | $R^2$ | Dose[a] μmol/kg | No. of mice | Median Survival Time[b] | T/C (%) |
|---|---|---|---|---|---|---|
| H | H | H | 0 | 10 | 9 | |
| | | | 17 | 10 | 13 | 144 |
| | | | 34 | 10 | 13 | 144 |
| | | | 51 | 10 | 15 | 147 |
| Ph | H | H | 0 | 10 | 8 | |
| | | | 17 | 10 | 10 | 125 |
| | | | 34 | 10 | 10 | 125 |
| | | | 51 | 10 | 2 | toxic |

TABLE 2-continued

Antitumor Activity of Oxazine Derivatives of
Cyclophosphazide Against L1210 Leukemia in BDF, Mice.

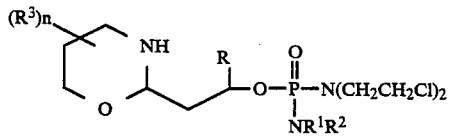

M = (CH₂CH₂Cl)

| Cmpd. R | R¹ | R² | Dose[a] μmol/kg | No. of mice | Median Survival Time[b] | T/C (%) |
|---|---|---|---|---|---|---|
| Ph | H | H |  | 12 | 8 |  |
|  |  |  | 17 | 11 | 10 | 125 |
|  |  |  | 34 | 11 | 12 | 150 |
|  |  |  | 51 | 11 | 12 | 150 |

[a]Compound was administered i.p. once, a day after inoculation of 5 × 10¹ cells.
[b]Days The values reported in Table 2 represent the percent increase in the survival time of L1210 leukemic mice treated with each drug compared with the survival time of untreated leukemic mice. A value <100% generally indicates that the survival time was shortened as a result of drug toxicity. A value of 125% is defined by the National Cancer Institute as the minimum value required to demonstrate antitumor activity; a value <150% is considered to represent substantial activity. As shown by invention exhibit in vivo antitumor activity.

The above preferred embodiments and examples are given to illustrate the scope and spirit of the present invention. These embodiments and examples will make apparent to those skilled in the art other embodiments and examples. These other embodiments are examples within the contemplation of the present invention. Therefore the present invention should be limited only by the appended claims.

What is claimed is:

1. A compound of the formula

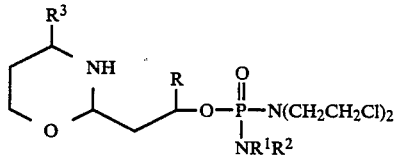

wherein R¹ and R² may be the same of different and are each independently hydrogen or lower alkyl which may be unsubstituted or monosubstituted with halogen or lower alkoxy or hydroxy with the proviso that the substituent is not on the α-carbon or R₁ and R₂ together with nitrogen to which they are attached from a morpholino ring;
each R³ is independently hydrogen, lower alkyl, carboxy or carbalkoxy;
n is an integer from 0, 1, 2 or 3 and
R is hydrogen, lower alkyl, cycloalkyl, arylalkyl aryl or a nitrogen, sulfur or oxygen containing heterocyclic or a heterocyclic lower alkyl and pharmaceutically acceptable salts thereof.

2. The compound according to claim 1 where R¹ and R² are the same or R¹ and R² taken together with the nitrogen to which they are attached form a morpholino ring.

3. The compound according to claim 1 wherein lower alkyl contains 1 to 3 carbon atoms.

4. The compound according to claim 2 wherein R is phenyl, pyridyl, hydrogen, ethyl or methyl.

5. The compound according to claim 2 wherein the R¹ and R² are substituted alkyl wherein the substituent is on the omega carbon or R¹ and R² taken together with the nitrogen to which they are attached form a morpholino ring.

6. The compound according to claim 5 wherein the substituent is chloro or ethoxy.

7. The compound according to claim 1 wherein R¹ and R² are independently hydrogen, methyl, $CH_2CH_2Cl$, $CH_2CH_2OCH_2CH_3$, $CH_2CH_2OH$ or R¹ and R² taken together with the nitrogen to which they are attached form a morpholino ring.

8. The compound according to claim 1 wherein n is 1 or 2.

9. The compound according to claim 1 having the formula

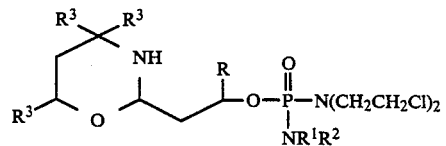

10. The compound according to claim 1 having the formula

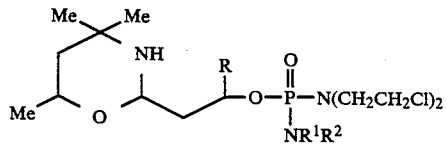

wherein each R₃ may be the same or different selected from the group consisting of lower alkyl.

11. A compound of the formula wherein R¹ and R² may be the same of different and are each independently hydrogen or lower alkyl which may be unsubstituted or monosubstituted with halogen, lower alkoxy or hydroxy with the proviso that the substituent is not on the α- carbon; or $R^1$ and $R^2$ taken together with the nitrogen to which they are attached from a morpholino ring, n is an integer from 0, 1, 2 or 3 and R is hydrogen, lower alkyl, cycloalkyl, arylalkyl aryl or a nitrogen, sulfur or oxygen containing heterocyclic or a heterocyclic lower alkyl and pharmaceutically acceptable salts thereof, and pharmaceutically acceptable salts thereof.

12. The compound according to claim 11 wherein lower alkyl contains 1 to 3 carbon atoms.

13. The compound according to claim 11 wherein $R^1$ is the same as $R^2$ or $R^1$ and $R^2$ taken together with the nitrogen to which they are attached form a morpholino ring.

14. The compound according to claim 13 wherein R is methyl, ethyl, phenyl, pyridyl or hydrogen.

15. The compound according to claim 14 wherein $R^1=R^2=$hydrogen, methyl or an omega substituted alkyl or $R^1$ and $R^2$ taken together with the carbon to which they are attached form a morpholino ring.

16. The compound according to claim 15 wherein the omega substituted alkyl is omega substituted ethyl.

17. The compound according to claim 16 wherein the omega substituted ethyl is $CH_2CH_2Cl$, $CH_2CH_2OCH_2CH$ or $CH_2CH_2OH$.

18. The compound according to claim 11 wherein
$R=R^1=R^2=$hydrogen;
$R=$hydrogen and $R^1=R^2=CH_2CH_2Cl$;
$R=$hydrogen and $R^1$ and $R^2$ taken together with the nitrogen to which they are attached form a morpholino group;
$R=$methyl and $R^1=R^2=$hydrogen;
$R=$ethyl and $R^1=R^2=$hydrogen;
$R=$phenyl and $R^1=R^2=$hydrogen;
$R=$phenyl and $R^1=R^2=CH_2CH_2Cl$; or
$R=$phenyl and $R^1$ and $R^2$ taken together with the nitrogen to which they are attached form a morpholino group;
$R=$phenyl and $R^1=R^2=CH_2CH_2OCH_2CH_3$.

19. A pharmaceutical composition comprising an effective amount of a compound according to claim 1 and a pharmaceutical carrier thereto.

* * * * *

UNITED STATES PATENT AND TRADEMARK OFFICE
CERTIFICATE OF CORRECTION

PATENT NO. : 4,908,356

DATED : March 13, 1990

INVENTOR(S) : Richard F. Borch, et al.

It is certified that error appears in the above-identified patent and that said Letters Patent is hereby corrected as shown below:

Column 2, line 11: "from to 10" should read as --from 6 to 10--

Column 2, line 39: "carbon These" should read as --carbon. These--

Column 4, line 37: "aldehyde, in accordance" should read as --aldehyde, RCHO, in accordance--

Column 7, line 11: "18" should read as --$\underline{18}$--

Column 7, line 14: ", 2970," should read as --3260, 2970,--

Column 7, line 46: "(P= )," should read as --(P=O),--

Column 9, line 17: "3.2" should read as --3:2--

Column 11, line 7: "(CDCl$_3$)" should read as --(CHCl$_3$)--

UNITED STATES PATENT AND TRADEMARK OFFICE
CERTIFICATE OF CORRECTION

PATENT NO. : 4,908,356

DATED : March 13, 1990

INVENTOR(S) : Richard F. Borch, et al.

It is certified that error appears in the above-identified patent and that said Letters Patent is hereby corrected as shown below:

Column 14, line 10: "(4.01g, was" should read as --(4.01g, 55%) was--

Column 19, line 30: "by invention" should read as --by the data in Table 2, the compounds of the present invention--

Column 22, line 5, Claim 5: "CH or" should read as --$CH_3$--

Signed and Sealed this

Eleventh Day of June, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,908,356
DATED : March 13, 1990
INVENTOR(S) : Richard F. Borch, et al.

It is certified that error appears in the above-identified patent and that said Letters Patent is hereby corrected as shown below:

Column 1, line 4, insert the following: --This invention was made with Government support under R01 CA 34619 awarded by the National Institute of Health. The Government has certain rights in the invention.--

Signed and Sealed this

Eighth Day of December, 1992

Attest:

DOUGLAS B. COMER

Attesting Officer

Acting Commissioner of Patents and Trademarks